US008460383B2

(12) United States Patent
Wirtel, III et al.

(10) Patent No.: US 8,460,383 B2
(45) **Date of Patent: *Jun. 11, 2013**

(54) INFLATABLE MULTI-CHAMBERED DEVICES AND METHODS OF TREATMENT USING THE SAME

(75) Inventors: Anthony Wirtel, III, Malvern, PA (US); Mark Borden, Collegeville, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/473,545

(22) Filed: May 16, 2012

(65) Prior Publication Data

US 2012/0232575 A1 Sep. 13, 2012

Related U.S. Application Data

(63) Continuation of application No. 11/761,069, filed on Jun. 11, 2007, now Pat. No. 8,236,057.

(60) Provisional application No. 60/804,505, filed on Jun. 12, 2006.

(51) Int. Cl.
*A61F 2/44* (2006.01)
*A61M 29/00* (2006.01)

(52) U.S. Cl.
USPC .......................................... 623/17.12; 606/192

(58) Field of Classification Search
USPC ................. 606/192, 90, 246, 249; 623/17.11, 623/17.12, 17.16; 604/101.01–101.03
See application file for complete search history.

(56) References Cited

U.S. PATENT DOCUMENTS

| | | | | |
|---|---|---|---|---|
| 6,220,908 | B1 * | 4/2001 | Peterson | 441/66 |
| 6,447,426 | B2 * | 9/2002 | Peterson | 482/27 |
| RE42,837 | E * | 10/2011 | Stoy et al. | 623/17.16 |
| 8,236,057 | B2 * | 8/2012 | Wirtel et al. | 623/17.12 |
| 2006/0149380 | A1 * | 7/2006 | Lotz et al. | 623/17.12 |

* cited by examiner

*Primary Examiner* — Katherine Dowe

(57) ABSTRACT

Inflatable multi-chambered devices are provided for repairing or replacing spinal discs and distracting neighboring vertebral elements. Also included are cushioning devices that may be used in a joint replacement device cushioning system. Further included are kits and systems that include such devices, methods for making such devices, and methods of treating patients in need of such devices. Examples further include cosmetic augmentation and restoration devices.

23 Claims, 11 Drawing Sheets

2
4
6
8
10
12

10 6 2 12 4 8
8 4 2 6 10

36
34

38
36
40

44
42

44
46
48

52
50
44
54

56
58
44
60
62

INFLATABLE MULTI-CHAMBERED DEVICES AND METHODS OF TREATMENT USING THE SAME

CROSS REFERENCE TO RELATED APPLICATION

This application is a Continuation of U.S. application Ser. No. 11/761,069 filed on Jun. 11, 2007 now U.S. Pat. No. 8,236,057 (allowed), which claims the benefit of U.S. Provisional Application No. 60/804,505 filed on Jun. 12, 2006; both of which applications are hereby incorporated by reference in their entireties.

FIELD

Example embodiments are generally directed to inflatable multi-chambered balloon devices, which may be useful for example, for the repair or replacement of spinal discs, as an inflation device to distract vertebral elements, as a cushioning device for joint replacement, or for cosmetic augmentation or restoration. Example embodiments are also directed to kits and systems that include such devices. Example embodiments are further directed to methods of treating a patient by inserting such devices into the patient.

BACKGROUND

The intervertebral disc (IVD) permits articulation between adjacent elements of the spine. The disc includes an outer annulus fibrosis and an inner nucleus pulposus. In a healthy disc, the nucleus is a gel that transmits load and absorbs shock. Loads are constrained axially by the annulus fibrosis. Through degenerative processes and/or trauma, the annulus may fail and release the nucleus, which is then free to flow.

The posterior annulus is typically thinner than the anterior annulus, thus, making failures of the posterior annulus more common. When these failures occur, a variety of problems may arise. For example, the contents of the disc may impinge onto nerve roots and/or the spinal cord, resulting in pain and/or neurological deficits. IVD failures in the lumbar region of the spine are most common, but failures can occur at any level.

When disc failure occurs and pain is present, discectomy may be indicated to remove the impinging material. A 5-10% recurrence of painful extrusion may occur. Loss of the nucleus leads to kinematic changes to the segment and can accelerate weakening of the annulus and development of osteophytes at the vertebral endplates. This development of ectopic bone may lead to stenosis of the vertebral canal and detrimental changes to other articulating elements.

Injected liquids and implants have been proposed for insertion into a spinal disc space for different purposes. For example, some proposed systems include inflated balloons to distract disc space to restore lost height as preparation for an injected biomaterial or as an implant. Other systems include injecting liquids that harden or thicken in situ or hydrogel systems that expand upon exposure to water. The use of such devices, however, shares a common weakness, in that a failure of the device would tend to lead to rapid expulsion of the filler material, for example, through a pre-existing defect in the annulus. Such expulsion may create impingement in the same area that created a need for surgical intervention in the first place. For example, failure of such a device may lead to loss of material from the disc space which may then impinge on neural elements. The loss of any material from such devices may lead to loss of disc height and detrimental changes to segment kinematics. Further, the arrangement of many of these devices would tend to lead to expulsion of the device itself, if deflated. Additionally, for devices constructed from a single chamber, the uneven compression of the disc in flexion and extension can result in improper loading of the disc space.

SUMMARY

Example devices are generally directed to multi-chambered devices, which may be useful as intervertebral disc nucleus pulposus augmentation or replacement devices, as inflation devices to distract neighboring vertebral elements, as cushioning devices for joint replacement, or for cosmetic augmentation, reconstruction or restoration. Examples may further include devices that may be useful in mechanical systems where damping is required, or to position or maintain the position, or isolate machinery or structures. Example devices may include inflatable balloon devices, which include at least two chambers and a filling manifold. Example devices are adapted such that at least one of the chambers, and preferably multiple chambers, may be filled with a filler material, for example after insertion of the device into a patient.

Example embodiments are also directed to kits and systems that include inflatable devices. Such kits and systems may further include various other items, including, but not limited to filler material, tools or devices for inserting the inflatable devices into a patient, and/or tools or devices for inserting the filler material into at least one chamber of the inflatable devices, such as a high pressure gun.

Example embodiments are further directed to methods of treating a patient in need of treatment, by inserting into the patient a deflated device, and then inserting at least one filler material into at least one chamber of the inflatable balloon device. Such methods may also include prior removal of all or part of a disc or other material at or around the location in the patient where the device is to be inserted.

DETAILED DESCRIPTION

Figure 1A:
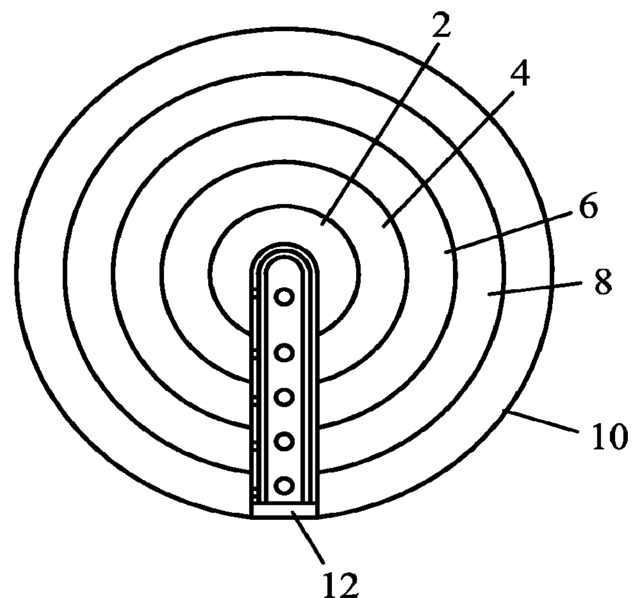
FIGS. 1A and 1B are top view and cross-sectional views respectively, of an inflatable device in accordance with example embodiments.

The aspects, advantages and/or other features of example embodiments will become apparent in view of the following detailed description, which discloses various non-limiting embodiments. In describing example embodiments, specific terminology is employed for the sake of clarity. However, the embodiments are not intended to be limited to this specific terminology. It is to be understood that each specific element includes all technical equivalents that operate in a similar manner to accomplish a similar purpose.

Example devices and methods may be used for many different purposes. For example, devices may be used to augment or to completely replace lost or degenerated nucleus pulposus of an intervertebral disc. Example devices may also be used as an inflation device to distract neighboring vertebral elements and restore proper anatomical height. Example devices may also be used as a total joint replacement device cushioning system, for example to reduce shock loading of articulating surfaces. The present devices may further be used for cosmetic augmentation or restoration, for example, in situations where providing multiple, isolated chambers to mitigate the loss of integrity of a single chamber may be advantageous. Examples may also have possible uses in mechanical systems where damping is required, or to position or maintain the position, or isolate machinery or structures (e.g., mechanical frame isolation, engine mounts, or earthquake protection for buildings).

Devices and methods according to example embodiments generally include a chambered balloon, or multiple balloons, which may distribute load placed on the device across each individual chamber. In example embodiments, load may be distributed substantially evenly. Various advantages of examples of the present devices and methods may vary depending on the desired use of the device. Non-limiting examples of advantages may include the following: Where the present devices are inflatable nucleus balloon devices being used as a replacement or augmentation of the nucleus pulposus, for example, if the device fails, the loss of integrity of a single chamber (or even possibly more than one chamber depending on the total number of chambers) would expel at most, only the amount of filler material that was initially used in the failed chamber(s). Because each chamber may be attached to at least one (in the case of an outermost chamber) and usually two or more neighboring chambers, failure of a chamber may be mitigated due to load sharing of neighboring chambers. That is, because the entire load bearing on the device will not be placed onto the failed chamber alone, but rather will continue to be held by neighboring chambers, less than all of the filler material in the failed chamber may be expelled. Additionally, in many of the present devices, the center of load may be essentially maintained, even if a chamber fails. Thus, if a single chamber fails, the overall height of the device may decrease somewhat, but there would be little or no adverse lean induced by the failure of the chamber. Where a single chamber failure occurs, the retention of other chambers limits the likelihood that the device itself may be ejected.

The present devices and methods may also be advantageous in embodiments where the device is being used to distract neighboring vertebral elements. In these example embodiments, because of the present multi-chamber load sharing designs, inflation of the device would tend to stress neighboring endplates more evenly and decrease local loading that may be possible with single balloon devices. Further, inflation of the present devices would allow a surgeon implanting the device into a patient to check the integrity of the annulus and other structures prior to committing to use of such a device as a permanent implant. For such use, the device could be used as an aid for alignment or sizing prior to use of other devices or approaches for spinal fusion. Similar and/or additional advantages may be realized when devices are being used for other purposes.

As used herein, “a” or “an” may mean one or more. As used herein, “another” may mean at least a second or more.

Unless otherwise specified, as used herein, the terms “device,” “inflatable device,” “inflatable balloon device,” “balloon device,” and the like, are used somewhat interchangeably herein to refer to inflatable multi-chambered devices provided herein. The term balloon includes any constructs such as bladders, tubes, or other contained chambers. When specified herein, the term “device” may be used to refer to other devices, such as devices useful in inserting or using the inflatable balloon devices.

The term “inflatable” as used herein is intended to mean that a device is capable of having a filler material inserted into the device, such as into one or more chambers or balloons, which may act to enlarge the volume of the device or one or more chambers or balloons thereof, from a deflated to inflated state. As discussed further below, these terms are intended to be relative with respect to each other and do not require absolute deflation or inflation. The terms “inflatable” and “balloon” and derivations thereof, are not intended to require that the device material be elastomeric or capable of stretching, although such possibilities are contemplated.

The terms “filled” or “inflated” are intended to mean that the device or chamber has filler material therein or added to it in a desired amount. These terms are not intended to mean that the device or chamber is necessarily entirely or 100% filled with a filler material (however, such embodiments are within the scope of the term “filled”). Similarly, a “deflated” device or chamber thereof does not necessarily mean that the device or chamber is entirely empty. There may be some air, or other filler material in a “deflated” chamber. A “deflated” device or chamber is intended to mean that the device or chamber does not include the filler material in an amount that would be desired after the device is filled.

The terms “fillers,” “filler material,” and “filling material” are used interchangeably herein to mean at least one material that may be inserted into at least one chamber of the present balloon devices. Non-limiting examples of suitable fillers may include for example, one or more gases (such as air), liquids (such as water, saline and the like), semi-liquids (such as hydrogels or in an in-situ setting polymer for example, an elastomeric material), and semi-solids. Example liquids may be curing (having the same or different viscosities before and after curing) or non-curing.

Example inflatable balloon devices generally include at least two chambers, and according to example embodiments at least three, four, five or six chambers or more. Devices further include at least one filling manifold, such as a valve or tube or other means through which filling material may be inserted into at least one of the chambers. By way of non-limiting example, generally encompassed are nucleus balloon devices, distraction devices, cushioning devices, plastic surgery devices, and damping, positioning and/or isolation devices that include at least two chambers; and at least one filling manifold.

Chambers may include independent chambers, interrelated chambers, or both. Independent chambers are chambers in which filler material does not pass between the chambers after they have been filled. For example, after filling, an opening in each chamber may be closed, such that even if material may have passed between the chambers prior to such closure, it does not pass between the chambers upon closing of the opening. It may be preferable to have at least two independent chambers, such that if leakage or breakage of a chamber occurs, at least one other chamber remains in tact without losing the filling material therein.

Filling manifolds or other means for filling at least one of the chambers with a filler material may include any apparatus or device that allows filler material to be inserted into at least one, and preferably inserted into at least two, of the at least two chambers. This may include for example, at least one way of providing access for a filler material to enter the at least one chamber.

The filling manifold may be further adapted such that it is capable of stopping filler material from entering or exiting the at least one chamber into which filler is inserted. Thus, the filling manifold or means for filling may have a device or method of closing off access to the chamber(s), for example, to prevent leakage of the filler material out of the chamber.

The filling manifold may be capable of shutting, sealing, or closing openings to the at least one chamber individually or substantially simultaneously. For example, the filling manifold may allow access to filling or emptying a single chamber, or more than one chamber, or all of the chambers simultaneously. Similarly, the filling manifold may allow the sealing of all chambers as independent units. As discussed further below, where more than one filling manifold is used, different combinations of chambers may be filled or sealed independently of others.

Optionally, the filling manifold, such as a ball valve, may have a locking mechanism to place or hold the valve in an open position or in the shut position when desired. According to example embodiments positive engagement (e.g., pushing in), may be required to fill chambers via a filling manifold, such as a ball valve.

Figure 1B:
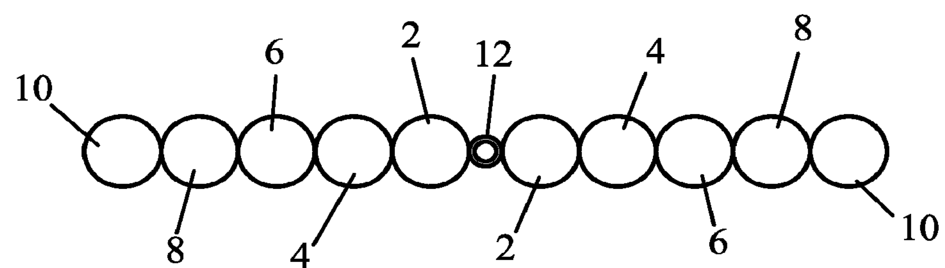

FIGS. 1A and 1B depict a top view and a cross sectional view, respectively, of non-limiting inflatable balloon devices constructed in accordance with example embodiments. FIG. 1A depicts an example device having a filling manifold and multiple chambers to allow for load distribution and limit the impact of possible failure of any particular chamber. As depicted in FIGS. 1A and 1B, example embodiments may include five independent chambers 2, 4, 6, 8, and 10, and a ball valve 12. The ball valve 12 allows for filling of each individual chamber.

Figure 2A:
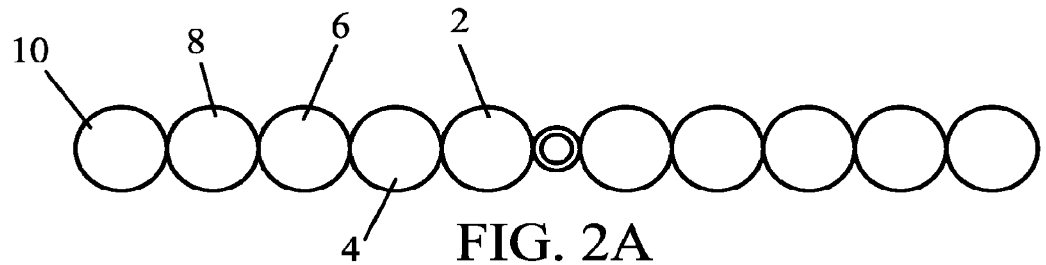
FIGS. 2A and 2B depict cross sectional views of an inflatable device in accordance with example embodiments.
Figure 2B:
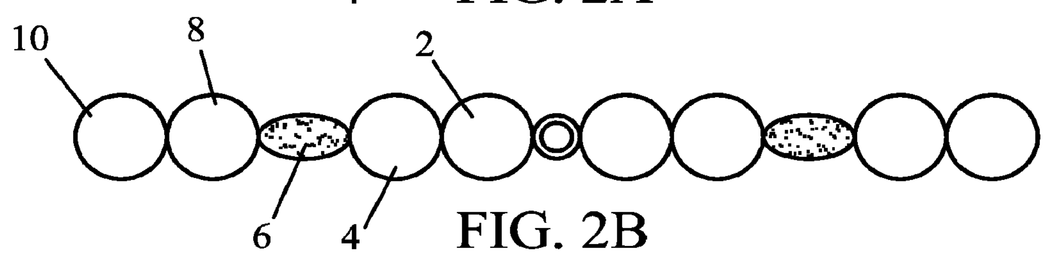

FIG. 2A depicts a cross section of an example of an inflatable balloon device in accordance with example embodiments, having five independent chambers 2, 4, 6, 8, and 10. FIG. 2A depicts a device in which all chambers of the device are inflated. FIG. 2B depicts the same device as FIG. 2A, but with a single chamber 6 having failed (see FIG. 2B). The failed chamber 6 is depicted in FIG. 2B as being deflated, having a smaller cross-sectional area, as such failure may result in the expulsion of filling material. As shown in FIG. 2B, the remaining chambers 2, 4, 8, and 10 remain intact, and may support whatever load is being placed on the device, even in the absence of the failed chamber's ability to support load. Example embodiments having more than one chamber are advantageous in that the rate and/or amount of outflow through a rupture may be reduced by virtue of having adjacent chambers that remain intact. Thus, it is possible that even upon failure of a chamber, some of the filler material initially inserted into the chamber may remain in the chamber, thus, reducing the volume of material ejected through a rupture and entering unintended portions of a patient's body cavity.

According to example embodiments, a filling manifold may have a single filling point. The use of a single filling point in a filling manifold or means for filling at least one of the chambers, may allow a relatively simple inflation of the device. If inflation is achieved through a single point leading to a manifold distributing fluid to individual chambers, a means to seal the chambers from neighboring units may be used.

By way of non-limiting example, a valve, such as a ball valve may be a suitable filling manifold or means for filling at least one chamber with a filler material. A rotating valve may have for example, a hole aligned with openings in each chamber such that when the valve is rotated to one position, the chambers may be filled or emptied, and when it is rotated to another position, the chambers are sealed. The valve may be capable of being shut to seal off the chambers after the at least one chamber is filled to a desired amount (which may be determined for example, by pressure or volume). The ball valve may be open or shut for example, by rotating the valve, e.g., 90 degrees. By way of further example, rotating the valve, e.g., 180 degrees may open or close a particular combination of chambers, such as a second and fourth chamber, and rotating the valve, e.g., 270 degrees may open or close a different combination of chambers.

Figure 3A:
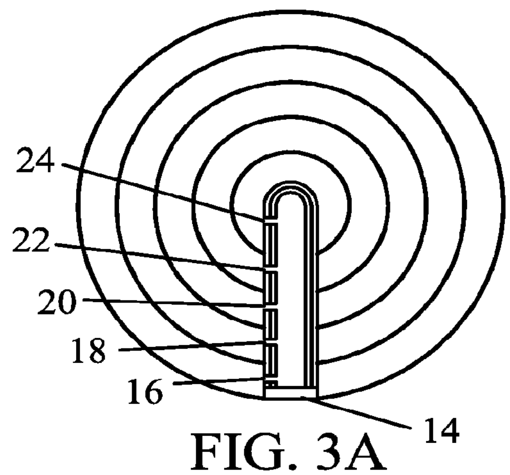
FIGS. 3A and 3B depict a top view of an inflatable device in accordance with example embodiments.
Figure 3B:
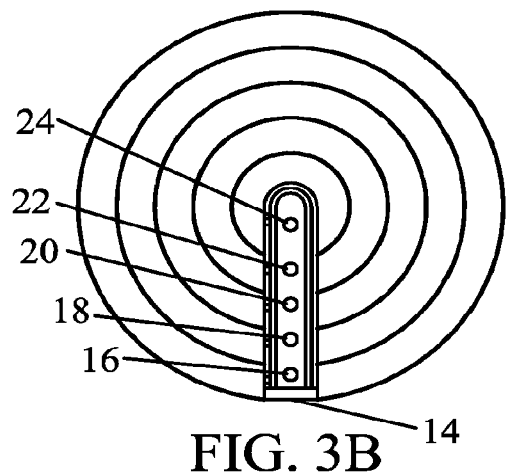

By way of non-limiting example, FIGS. 3A and 3B depict example embodiments in which a rotating valve is used as the filling manifold. As depicted in FIG. 3A, a valve 14 is rotated to a position such that holes 16, 18, 20, 22, and 24 in the valve are aligned with corresponding openings in the chambers, such that filling material may be inserted through the valve into (or withdrawn from) each of the chambers of the device. FIG. 3B depicts the same device as FIG. 3A, however in FIG. 3B, the valve 14 is rotated into a position such that the holes 16, 18, 20, 22, and 24 in the valve are not aligned with openings in the chambers and filling material may not be inserted into at least one chamber through the valve, escape through the valve, or travel from one chamber to another through the valve.

The use of multiple filling points, for example by use of multiple filling manifolds, is also contemplated. Multiple filling points may simplify the device and may also serve to reduce the risk of whole device failure in the event of a single-point filling manifold failure. According to example embodiments in which the device has for example, four chambers, there may be two filling manifolds, each allowing the filling of two chambers. Each manifold may then be sealable, as in the single filling point method.

Figure 4:
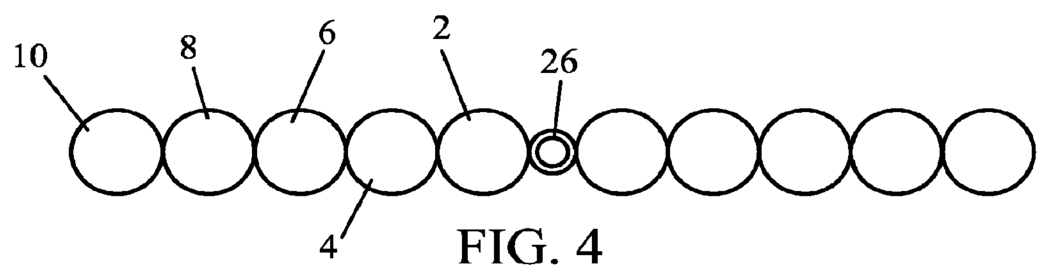
FIG. 4 depicts a cross sectional view of an inflatable device in accordance with example embodiments.
Figure 5:
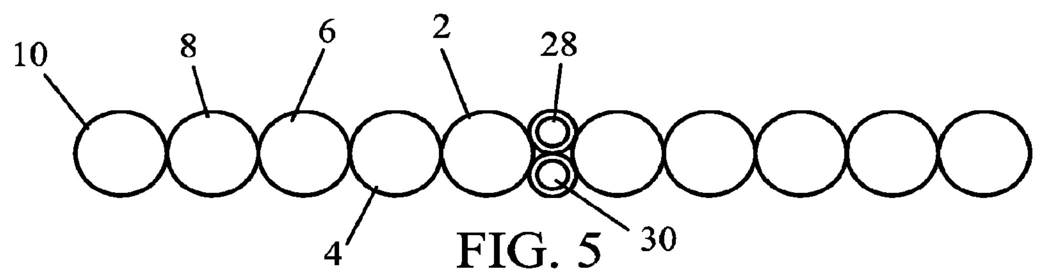
FIG. 5 depicts a cross sectional view of an inflatable device in accordance with example embodiments.

As depicted in FIG. 4, a single filling manifold 26 may be used to fill any or all of the chambers 2, 4, 6, 8, and 10. FIG. 5 depicts embodiments having multiple filling points, e.g., through multiple filling manifolds 28 and 30. In these example embodiments two filling valves are used to fill any or all of the chambers 2, 4, 6, 8 and 10. Depending on the arrangement of openings in the filling manifolds 28 and 30, either filling manifold may be used to fill all of the chambers (for example, if filling manifold 30 is used as a back-up device with the same capabilities to fill all of the chambers that filling manifold 28 has), or the different filling manifolds may be used to fill different chambers (for example, filling manifold 28 may be used to fill chambers 2, 6 and 10, while filling manifold 30 may be used to fill chambers 4 and 8).

As discussed further below (see for example, FIGS. 7-12), the present embodiments are not limited to the use of one or two filling manifolds. Additional filling manifolds may be present and used, for example, as backup devices with the ability to fill all chambers, or used to fill various single chambers or combinations of chambers.

In embodiments in which the filler material includes e.g., gases, liquids, and semi-liquids, a filling manifold that is not permanently sealed may advantageously offer the ability to open and drain the device, for example in the event that the device needs to be removed. Rotating valves, such as those discussed above, and as depicted for example in FIGS. 3A and 3B, are non-limiting examples of filling manifolds or means for filling that may not produce a permanent seal, and thus, allow the possibility of further filling of the device, and/or the ability to open and drain the device.

As indicated above, valves are only examples of filling manifolds or means for filing. Alternative filling manifolds or means for filling at least one chamber are also contemplated. For example, such an alternative means may include tubes that may be sealed by a variety of methods, including, mechanically or through heat. Other embodiments may also include sealing the filling manifold(s). By way of non-limiting example, sealing methods may include heat (e.g., laser, hot melting, ultrasound, and RF), mechanical plug (e.g., friction, screw, plug, crimp with a metal or other device, and suture), chemical (e.g., adhesive) and by friction (e.g., stir weld). Other sealing methods may include for example one way check valves that may be self-closing or self-sealing. Example embodiments may permanently seal the chamber (s). According to example embodiments, such a valve may be used to seal a single chamber or multiple chambers.

Chambers and/or balloons of the devices may be made of any suitable material for insertion into the body. Each chamber generally includes space in which to fill the chamber with at least one filler or filler material. Chambers and/or other components of the devices may be for example, flexible or semi-rigid. It may be advantageous that a chamber is flexible enough to be able to condense, collapse, or compress down in size when it is in a deflated state, such that it is smaller (than in an inflated state) for insertion into a patient. For example, devices in accordance with example embodiments may be flexible enough such that they can be deflated or collapsed small enough to permit insertion of the device into a patient through a small cannula. According to non-limiting example embodiments, prior to insertion into a patient, a multi-chambered implant device can be folded or rolled in such a manner as to allow delivery of the device using minimally invasive surgical equipment such as tubes or cannulas.

According to example embodiments, devices may be constructed of a flexible polymer that permits high loading. According to example embodiments, chambers may be made of a material that permits connection of neighboring chambers. Thus, according to example embodiments devices may include chambers that are attached to one another by a means of attachment. Non-limiting examples of the means of attachment may include for example, welding, use of adhesives, or molding. According to example embodiments, outside walls of the chambers are attached to each other, either completely or partially (for example where an adhesive connects outside walls of at least two chambers together along strips, edges or points). The device may also be constructed from a single chamber that is subdivided into separate chambers through the use of baffles or other dividing structures. The subdivided chambers may be independent from one another or may be connected.

According to example embodiments, devices may be constructed of semi-independent rings (or other shapes) attached at a central body.

Figure 6:
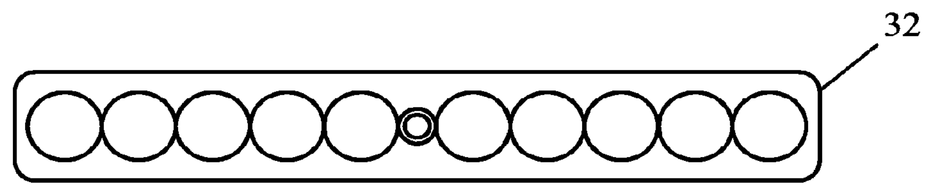
FIG. 6 depicts a cross sectional view of example embodiments of devices having an encasement around the device.

According to example embodiments, devices may be encased in a sheath 32, as depicted for example in FIG. 6. The sheath may be a separate sheath made of the same or different material as a balloon and/or one or more chambers of the device. The sheath may be for example, a flexible sheath made from any suitable material, such as a sheet material, whether continuous, woven, braided, or a combination thereof. Sheet materials may include for example, natural and/or synthetic polymers. The sheath may be a reinforcing material. Thus, according to example embodiments, devices may include at least two independent chambers surrounded by reinforcing material, such as a mesh or braid. According to example embodiments, the sheath may not prevent the chambers or the device as a whole from reducing size when it is in a deflated state (for example for insertion into or removal from a patient).

Chambers may be any suitable shape (round, oval, square, rectangular, trapezoidal, honeycomb, or other shapes) (see for example, FIGS. 7-12) and/or size depending on the desired insertion location and purpose within a patient. Although cross-sectional shape variations are depicted in FIGS. 7-12, variations in size and/or shape occur in all dimensions and may relate for example, to the shape or size as seen from a top view as well. Suitable variations of the cross section may permit for example, restoration of lordosis or kyphosis in a patient. According to example embodiments (see e.g., FIGS. 18A-18B), the device may be shaped in such a way as to correct for abnormal curvature and/or restoration of normal curvature of the spine.

Figures 7, 8, 9, 10, 11, 12:
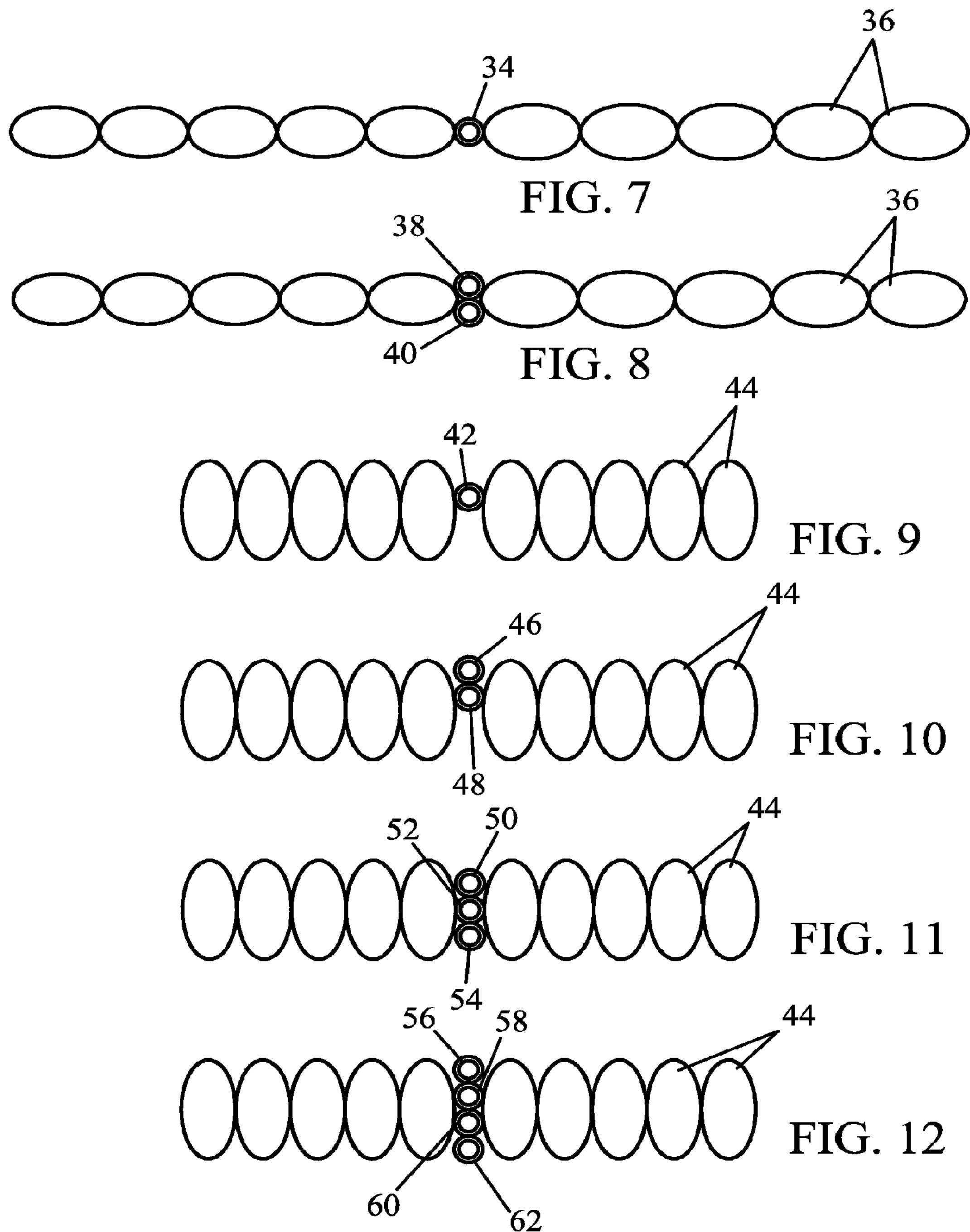
FIGS. 7-12 depict cross sectional views of example embodiments of devices, in which chambers have oval cross sections and are oriented in different directions.

FIGS. 7-12 depict example embodiments in which a cross-sectional view of the chambers are essentially oval in shape. The chambers may be positioned with the ovals 36 end to end as depicted in FIGS. 7 and 8, or with ovals 44 side to side, e.g., with the flatter part of the ovals touching one another as depicted in FIGS. 9-12. The embodiments depicted in FIGS. 8, 10, 11 and 12 may be advantageous for example, in embodiments where more than one filling manifold is desired for filling or emptying the chambers. FIGS. 7 and 9 depict embodiments having one filling manifold 34 and 42. FIGS. 8 and 10 depict embodiments having two filling manifolds each (38 and 40 in FIGS. 8, and 46 and 48 in FIG. 10). FIG. 11 depicts embodiments having three filling manifolds 50, 52 and 54, and FIG. 12 depicts embodiments having four filling manifolds 56, 58, 60 and 62. It should be recognized that the shape, size and number of chambers, and the shape, size and number of filling manifolds can all be varied.

Figure 13:
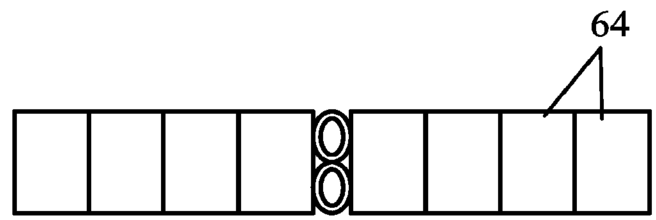
FIG. 13 depicts a cross sectional view of example embodiments of devices, in which chambers are essentially rectangular upon inflation.
Figure 14:
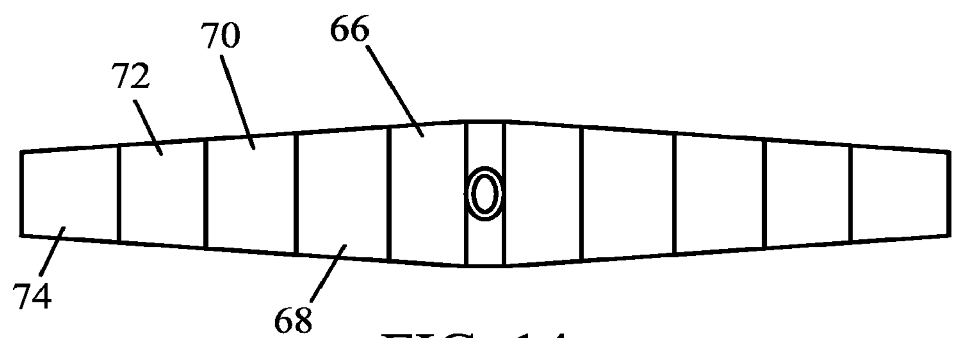
FIG. 14 depicts a cross sectional view an inflatable device in accordance with example embodiments, in which chambers have various shapes upon inflation.
Figure 15:
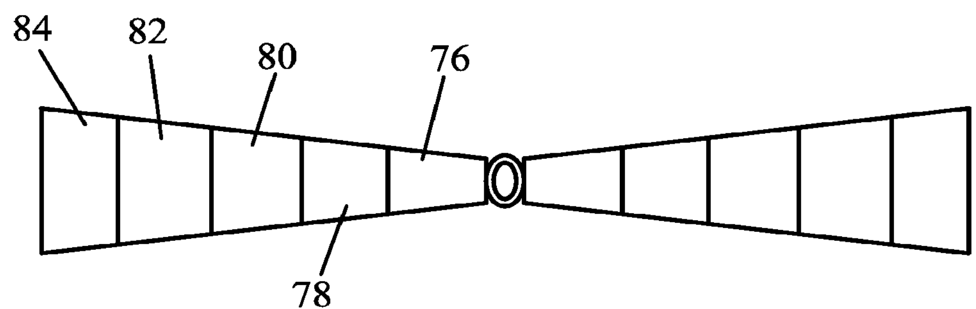
FIG. 15 depicts a cross sectional view of an inflatable device in accordance with example embodiments, in which the chambers have various shapes upon inflation.

FIG. 13 depicts other example embodiments in which the cross sections of the chambers 64 are similar in size and shape to one another and are generally rectangular in shape. FIGS. 14 and 15 depict embodiments in which the cross-sections (66, 68, 70, 72 and 74 in FIGS. 14, and 76, 78, 80, 82 and 84 in FIG. 15) of the chambers vary in shape and form a desired shape, for the intended use of the device, for example for insertion into a particular location in a patient.

Figures 16A, 16B:
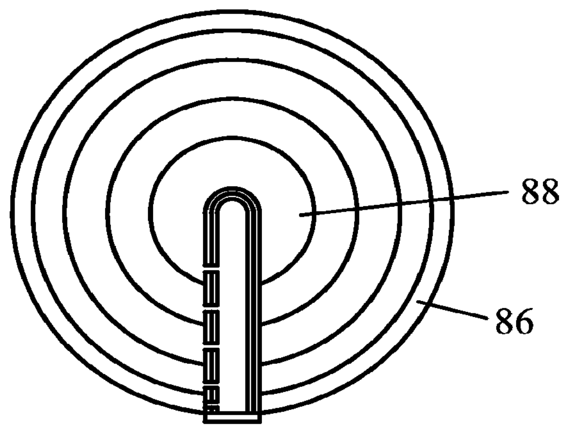
FIGS. 16A and 16B depict a top view and cross-sectional view, respectively, of example embodiments of devices, in which the chambers are designed such that each chamber may contain approximately the same volume of filler material.

According to example embodiments, chambers are designed such that each chamber may contain approximately the same volume of filler material. FIG. 16A depicts a top view of an example of such embodiments, and FIG. 16B depicts a cross-sectional view. As shown in FIG. 16A, when viewed from the top, the outermost chamber 86 has a greater circumference than innermost chamber 88. Therefore, as depicted in FIG. 16B, the outermost chamber 86 may be designed to have a generally smaller cross-sectional area than the innermost chamber 88 to arrive at a total volume of the outermost chamber that is approximately equivalent to the total volume of the innermost chamber. The term "volume" or "total volume" as used in this context is intended to mean the total space within a chamber in which filler material may be inserted.

In example embodiments, the orientation of the chambers may vary depending on the desired insertion location and purpose. For example, according to non-limiting embodiments, chambers may be stacked upon one another, and/or oriented in parallel or in series.

Figure 17A:
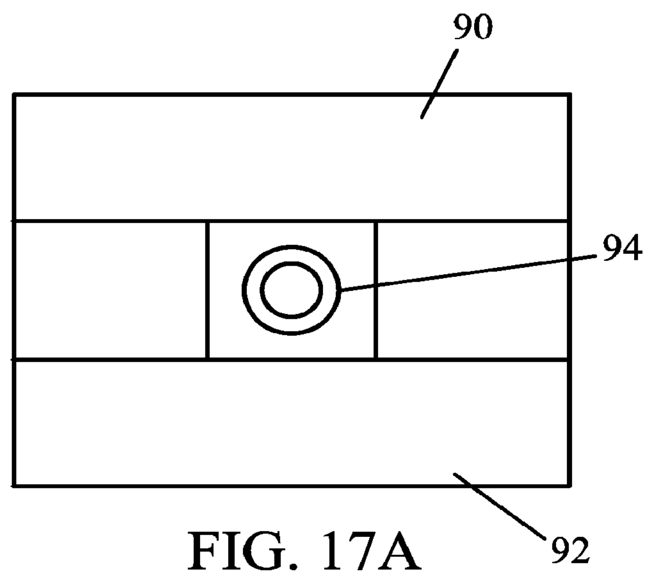
FIGS. 17A and 17B depict front and top views, respectively, of an inflatable device in accordance with example embodiments, having a stacked chamber design.
Figure 17B:
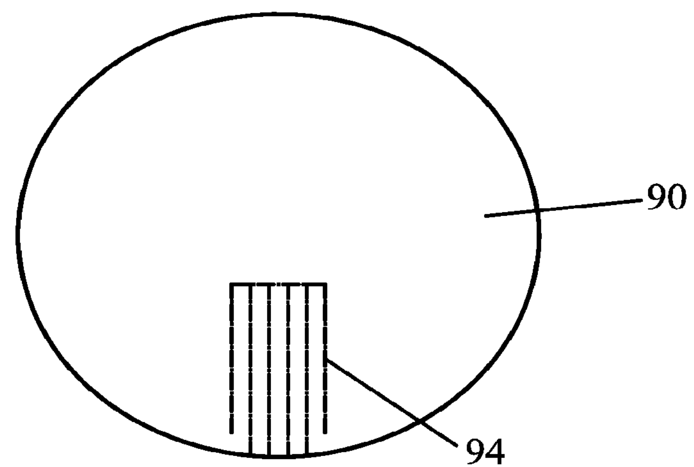

FIG. 17A depicts a front view of an example embodiment having chambers (such as balloons) stacked upon one another. According to the depicted example chambers 90 and 92 are substantially parallel to one another on opposite sides of a central fill valve 94. FIG. 17B depicts a top view of this example embodiment, showing the central fill valve 94 by way of phantom lines.

Figure 18A:
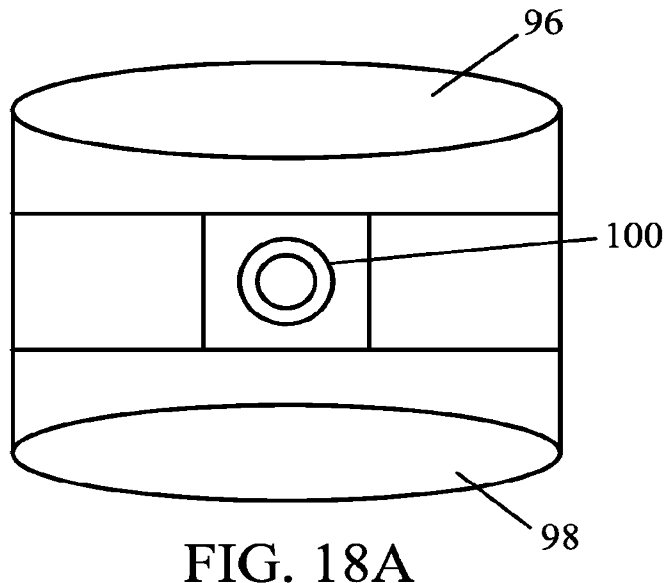
FIGS. 18A and 18B depict front and side views, respectively, of an inflatable device in accordance with example embodiments, having a stacked chamber design.
Figure 18B:
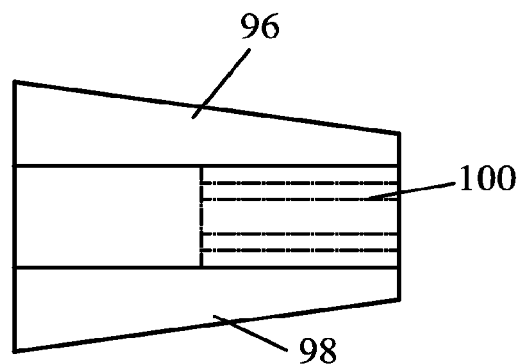

FIG. 18A depicts a front view of another example embodiment having chambers (such as balloons) stacked upon one another. According to the depicted example embodiment, chambers 96 and 98 have non-parallel top and bottom chambers on opposite sides of a central fill valve 100. FIG. 18B depicts a side view of this example embodiment, showing the central fill valve 100 by way of phantom lines.

Numerous possible stacked designs in addition to those depicted herein are contemplated, including designs having various numbers of chambers in varying sizes, shapes (e.g., round, oval, square, rectangular, trapezoidal, honeycomb, etc), and configurations.

Figure 19:
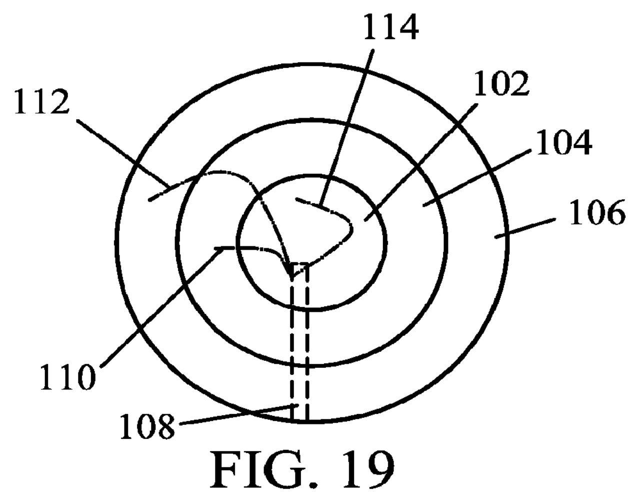
FIG. 19 depicts a cross-sectional view of an inflatable device in accordance with example embodiments having tubes for filling each chamber.
Figure 20:
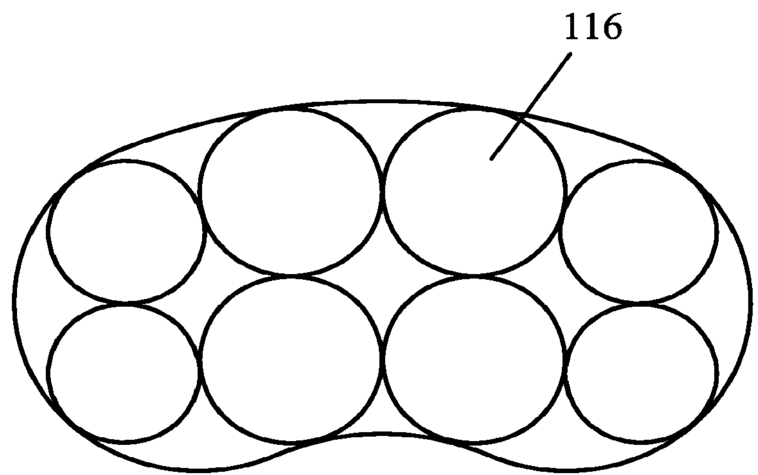
FIG. 20 depicts of a cross-sectional view of an inflatable device in accordance with example embodiments.
Figure 21:
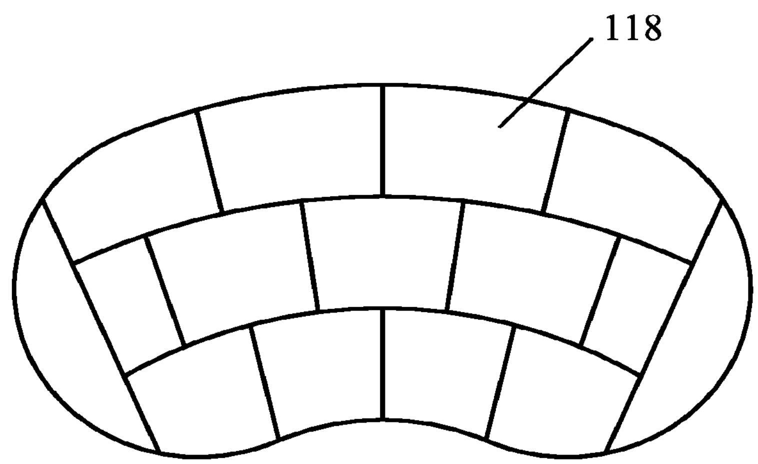
FIG. 21 depicts of a cross-sectional view of an inflatable device in accordance with example embodiments.
Figure 22:
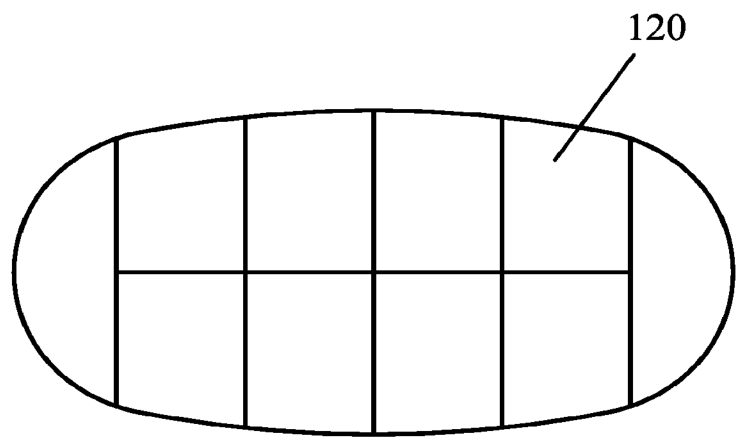
FIG. 22 depicts of a cross-sectional view of an inflatable device in accordance with example embodiments.
Figure 23:
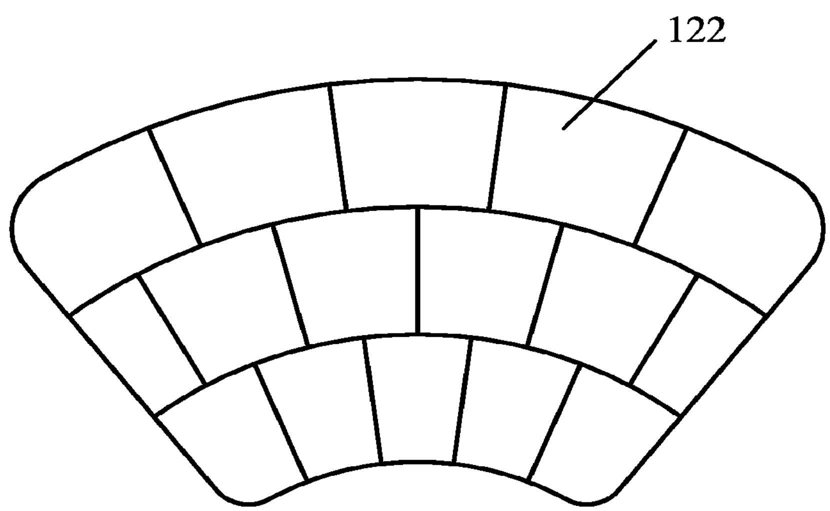
FIG. 23 depicts of a cross-sectional view of an inflatable device in accordance with example embodiments.

FIG. 19 depicts a top view of another example device. As depicted in FIG. 19, example embodiments may include multiple independent chambers 102, 104 and 106, which in this particular embodiment are annular rings without a break for a valve. According to the depicted example embodiments, a tube 108, which has several branches 110, 112, and 114, allows for filling each individual chamber. The tube 108 may be in any number of positions, such as above or below the annular rings. Advantages of these embodiments may include a smaller fill profile, and potentially simpler fabrication, because any need for attachment of a valve to tubes (such as in other possible embodiments), would be eliminated. These example embodiments may also be advantageous in permitting greater contact of inflated rings in space that may be occupied by a valve in other embodiments.

FIGS. 20-23 depict cross-sectional views of various example embodiments having chambers 116, 118, 120, and 122, respectively, in various sizes, shapes and configurations. The devices themselves may also be of various sizes and shapes. As with other embodiments herein, the chambers of these embodiments may be connected to other chambers in the same device (such as bonded to one another) or independent from one another. According to example embodiments, a single filling port can be connected to each chamber via a filling tube (not shown in FIGS. 20-23). According to further example embodiments, a one-way valve on each chamber may separate the chambers from one another.

Figure 24A:
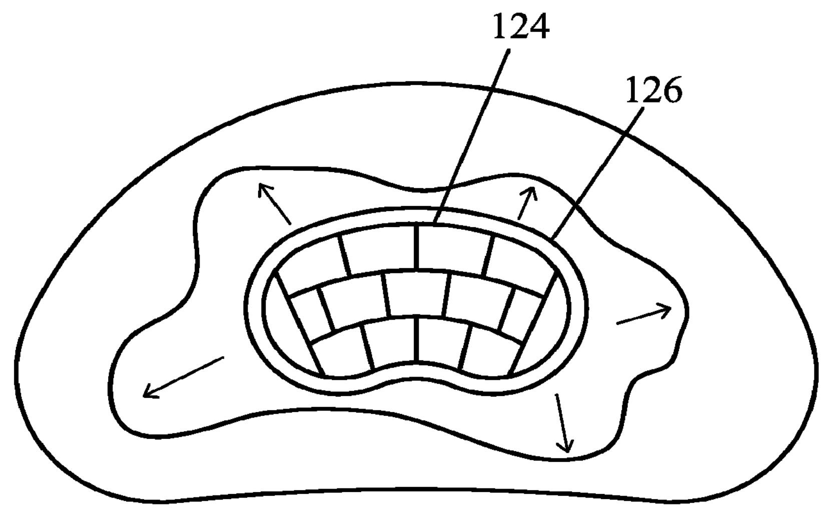
FIGS. 24A and 24B depict cross-sectional views of an inflatable device in accordance with example embodiments, before and after an outer chamber is expanded.
Figure 24B:
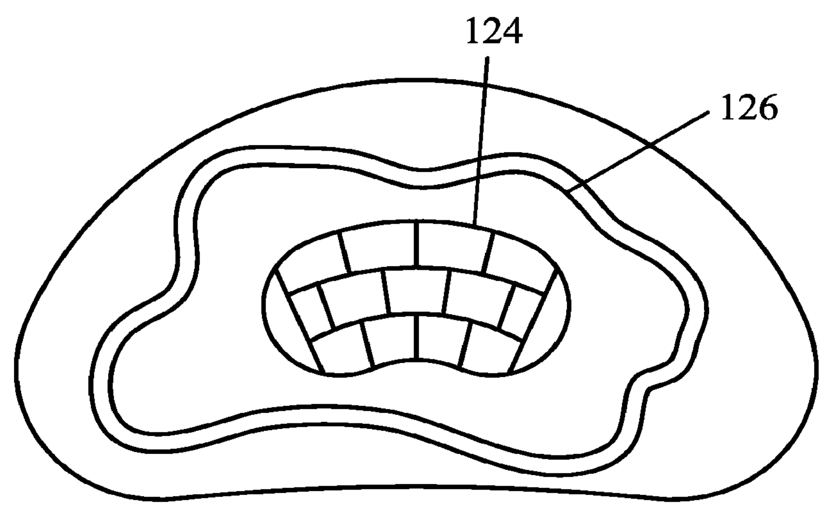

According to example embodiments, at least two chambers are surrounded by an outer balloon or film. The outer balloon or film may be designed to be capable of providing a custom fit to a surgical site. By way of non-limiting example, FIGS. 24A and 24B depict a multi-chambered balloon 124 surrounded by an outer balloon 126. The outer balloon may be highly elastic. Using a filling port, the outer balloon 126 may be filled, such that it may position or hold the multi-chambered balloon in a desired location, such as substantially at the center of a disc. FIG. 24A depicts the example embodiment before the outer balloon 126 is filled and expanded, and FIG. 24B depicts the example embodiment after filling and expansion of the outer balloon 126.

In accordance with example embodiments, devices may further include the filler material itself. Example filler material may advantageously possess similar properties to material being replaced. For example, in embodiments where the device is being used for the replacement or augmentation of nucleus pulposus, the filling material may possess similar properties to nucleus pulposus after being inserted into devices.

In embodiments where the device is to be inserted into a patient, the filler material may be a resorbable material that would be relatively quickly absorbed by the site if a rupture of any part of the device occurs, thus, releasing filler material into the body cavity of a patient. According to example embodiments, a fast resorbing filler material may be used, such that any impingement on any surrounding nerve tissue (in the case of rupture of a chamber) would likely be temporary. Example fillers may be degradable or non-degradable.

Advantages may be obtained by using a reverse phase gel as the filler material for embodiments where the device is for implantation into a patient. Reverse phase gels are liquid at room temperature and set into a higher viscosity gel once exposed to a higher temperature, such as body temperature. These types of gels could be relatively easily injected into chambers of the device in a liquid state or at least in a state that has lower viscosity than after insertion (for example, at room temperature), and thus, minimize filling pressures. Once injected, the filler material would warm to body temperature, and a gel with improved mechanical properties would form. According to example embodiments, a phase change to this or other filler material may take place by a change in pressure, pH, light exposure, temperature change and/or other factors.

In the gel state, the filler material would be less likely to rupture the balloon chambers and migrate away from the implant device, than other filler materials (e.g., liquid or gas filler materials). A non-limiting example of such gel fillers may include for example, a hydrogel, such as a non-resorbable hydrogel that is liquid at room temperature, but gels at body temperature. Example hydrogels may include one or more components. Example embodiments may include hydrogels for which a phase change may be initiated by pressure, pH, light exposure and/or temperature.

The degree to which a particular chamber has been filled may be determined for example, by pressure or volume. For example, a pressure gauge in or on the device may be used to determine if one or more of the chamber(s) are filled or deflated to a desired amount. Accordingly, example devices may further include a pressure gauge, or a transducer capable of transmitting pressure as a signal to a remote readout, or other means of detecting the pressure and/or volume in a chamber. According to example embodiments, the filling end point is based on pressure rather than on volume, which may be advantageous in the event that the disc space is filled before the device is filled (e.g., when a device is selected that has a capacity larger than the space it is filling, or when nucleus material remains in the disc space). According to example embodiments a sensor may be embedded in the device or externally in the filling system, to allow measurement e.g., of pressure when combined with a suitable readout for the sensor.

The filling manifold may be adapted such that the chamber being filled may be manually or automatically closed off after it is filled to a desired amount or to a desired pressure.

Example devices may further include the use of a radiolucent or radiopaque balloon film or filler material. By including radiolucent or radiopaque dyes in the implant devices and/or in the filler material, the device's position for example, during placement into a patient, may be visualized on a radiographic image. Such visualization may help in determining if the implant is properly inflated and/or properly positioned for example within a patient. For example, visualization may help determine if the implant is properly positioned within the patient's nucleus cavity.

According to example embodiments, devices may be constructed such that there is little or no protrusion from the device, for example, in the way of valves and inlets. Such a design may be advantageous, for example, in limiting the possibility that the device or elements thereof may impinge on neural elements.

According to non-limiting example embodiments, a nucleus replacement device for an intervertebral disc is provided, which includes a multi-chambered inflatable balloon made of a flexible material; at least one filling manifold adapted to allow a filler material to be inserted into at least one of the chambers via the filling manifold; a pressure detector adapted to detect pressure within at least one of the chambers; and a sealing means to prevent the filler material from entering or exiting at least one of the chambers.

Also included are methods of making inflatable devices provided herein.

Further included are kits that include at least one inflatable balloon device, which have at least two chambers and at least one filling manifold or other means for filling at least one of the chambers. Kits may further include one or more devices, tools, materials and the like that may be included in or with the inflatable balloon device (e.g., the material to be inserted therein, pressure gauge, transducer, radiolucent and/or radiopaque dye, etc. . . . ). According to example embodiments, kits may include one or more devices, tools, materials and the like which may assist in inserting the device into a patient and/or extracting the device from a patient. It may be advantageous to use a single instrument that may be used for placement and filling of the device.

According to example embodiments, kits may include devices, tools, materials, etc. which may be useful in inserting filler material into the device (e.g., a high pressure gun), or for removing filler material from the device. Kits may include at least one component for determining when a desired filling point has been achieved. Kits may further include devices, tools, materials, etc., which may be used for opening the manifold(s) or chamber(s), (such that filler material may be inserted into or removed from the device), or for closing the manifold(s) or chamber(s), (such that material does not escape (e.g., a tool for rotating the filling manifold)).

Kits may also include tools or devices that may be useful in preparing a patient for insertion of the device into the patient (such as tools for removing a spinal disc or portions thereof prior to insertion of the device).

Kits may include at least one component for visualizing the device within a patient.

Example embodiments are further directed to methods of treating a patient, which include inserting into a patient in need of treatment, an inflatable device, such as those described herein. Methods may include for example, inserting the device into a patient (for example through a tube or cannula), where the device is in a deflated state and then inflating the device after insertion, for example, by inserting a filler into at least one chamber of the device. Example methods where the device is inflated or expanded within a particular location of a patient, such as within the disc space, may be advantageous for example with respect to minimizing any likelihood of device ejection.

A patient in "need of" treatment is intended to encompass situations in which treatment is medically necessary, as well as where treatment is medically advisable, or where treatment is desired but optional. For example, the patient may be in need of intervertebral disc nucleus pulposus augmentation or replacement, may have a need for a device that may require distraction of neighboring vertebral elements, may be in need of joint replacement, and/or may be in need of cosmetic augmentation or restoration.

According to example embodiments, when devices are replacing a disc or portion thereof, a disc or portion thereof may be removed from the patient prior to insertion of the device. For example, the nucleus pulposus may be substantially or completely removed from a patient, a deflated balloon device inserted into the new substantially empty nucleus cavity, and the balloon device inflated to a desired amount. By way of example, the balloon may be inflated until the nucleus space is filled, or to some other desired amount.

Example methods may further include closing openings in the device, such as in the chamber(s) or the filling manifold or means, such that filler material does not escape or leak out of the one or more chambers, or travel between chambers after the chambers are filled. By way of non-limiting example, in embodiments where the balloon device includes a ball valve, the valve may be shut by rotating the valve after inflation of the chambers to the desired pressure and/or volume.

Example methods may also include ensuring that primarily or only desired material is introduced into the device.

According to example embodiments, before performing or as part of methods, it may be advantageous to inject a substance, such as a dye into the patient, for example, into the nucleus to determine for example, the degree and/or location of damage, such as damage to the spinal disc. Diagnostic procedures currently being used to determine the degree of damage of a spinal disc may include for example, placing a needle in the nucleus and injecting a dye for fluoroscopic visualization. As would be apparent to those skilled in the art, other diagnostic procedures may be utilized in the example methods, which may be suitable to assist these methods. By way of non-limiting example, diagnostic procedures encompassed by the present methods may include those that determine the degree or location of damage, or those that may assist in positioning the device or determining the amount of filling. The information obtained from such a procedure may assist in the selection of the particular device for insertion (e.g., size or shape of the device; number, shape and/or size of chambers; etc.) and/or the type or amount of filler used (e.g., whether to use air or hydrogel, to what height, volume or pressure to fill the chambers, etc).

Example methods may include removing a device, as described herein, from a patient, which includes removing filler material from the device in the patient, deflating the device (which may automatically occur upon removal of the filler material), and extracting the device from the patient.

Example embodiments are further directed to systems that may include an inflatable balloon device as described herein, and at least one additional component, such as those that may be suitable for inclusion in kits discussed herein, such as the filler material itself. Systems may also include pressure gauges, transducers, or other means for determining the amount of filling inserted into the device and the like. Systems may include means for visualization of devices, such as computers, computer monitors and any other components that may be useful for such visualization.

According to example embodiments, the present devices may be cushioning devices, which may be used for example, as part of a total joint replacement device cushioning system. Cushioning may advantageously reduce impulses transmitted through total joint bearing materials, and may help restore functional shock absorption that may be lost with damage or removal of articulating cartilage. Such damping may be of particular use where metal-on-metal, metal-on-ceramic, or ceramic-on-polymer articulations are currently used. Damping may be useful for traditional metal-on-polymer designs as well, to reduce the effect of shock loading seen on relatively small contact areas, as is the case for example, with total knee, ankle and shoulder replacements. Cushioning devices may be useful for example, with respect to any area where joints are replaced, including, but not limited to, spine, wrist, fingers, and toes.

Devices in accordance with these example embodiments may be tailored by those skilled in the art having reviewed this disclosure specifically for use as a cushioning device, for example, as part of a total joint replacement device cushioning system. It would be apparent to those skilled in the art that the filler material in such a cushioning device may be different than a filler material used in devices e.g., for distracting neighboring vertebral elements. Similarly, those skilled in the art would be able to determine the appropriate shapes and sizes of suitable devices for use as a total joint replacement cushioning system, and that such shapes and sizes may be different from those of devices used for different purposes.

Accordingly, examples include cushioning devices having at least two chambers; and at least one filling manifold adapted to allow a filler material to be inserted into at least one of the at least two chambers via the filling manifold. Further embodiments include systems and kits that include such devices. Systems and kits may further include one or more devices, tools, materials and the like that may be useful with respect to joint replacement and methods of performing joint replacement.

Further included are methods of replacing a joint, which include inserting into a patient in need of joint replacement, at least one cushioning device that includes at least two chambers; and at least one filling manifold adapted to allow a filler material to be inserted into at least one of the at least two chambers via the filling manifold. Such methods may further include one or more steps that would be useful in joint replacement or other methods where a cushioning device would be used. For example, methods may include removal of cartilage or other components prior to insertion of the device into a patient.

These example embodiments may include other aspects as described herein, which would be apparent to those skilled in the art reading this disclosure.

It is also contemplated that the present devices may be devices adapted for plastic surgery augmentation, reconstruction, restoration, and/or tissue expansion. For example devices may be cosmetic devices used in areas of the body where filled implants are typically used, e.g., tissue expanders, cheek implants, gluteal implants, breast implants, etc. . . . Accordingly, also included are plastic surgery and reconstruction implant devices that include at least two chambers; and at least one filling manifold adapted to allow a filler material to be inserted into at least one of the at least two chambers via the filling manifold. These example embodiments may include other aspects as described herein, which would be apparent to those skilled in the art reading this disclosure. For example, in these example embodiments, it may be particularly advantageous to not have the filling manifold (e.g., valve) extruding from the device, or be visible or palpable in any way.

Also included are kits and systems including such implants and methods of treatment that include inserting such implants into a patient in need thereof.

It is also contemplated that the present devices may be used as damping devices in mechanical systems where damping is required or to position or maintain the position, or isolate machinery or structures (e.g., mechanical frame isolation, engine mounts, earthquake protection for buildings). The present fillable devices may be useful in such mechanical systems, for example, for purposes of simplified installation, replacement, and/or maintenance.

Accordingly, example embodiments are directed to damping devices that include at least two chambers; and at least one filling manifold adapted to allow a filler material to be inserted into at least one of the at least two chambers via the filling manifold. Such devices may optionally incorporate sensors (for example, to measure position, pressure, temperature, etc.). An advantage of using such devices in these applications may include the ability to tailor chamber cross section (s) and orientations (e.g., stacked, used in parallel or series) for intended use. Just as with other embodiments, the present devices are advantageous in that the failure of a chamber would not lead to total system failure. Further included are kits and systems including such devices, and methods for their use.

These example embodiments may include other aspects as described herein, which would be apparent to those skilled in the art reading this disclosure.

The following example illustrates specific embodiments. The example set forth herein is meant to be illustrative and should not in any way serve to limit the scope of the claims. As would be apparent to skilled artisans, various changes and modifications are possible and are contemplated, and may be made by persons skilled in the art.

EXAMPLE

This prospective example sets forth a method for replacing the nucleus pulposus in a patient, using example devices. A patient having a spinal disc defect is prepared for surgery and the nucleus pulposus of the patient is removed. A device is selected, based on various factors, which may include for example, the size and shape of the cavity to be filled and the relative load to be placed on the device. According to this example, a device having five independent inflatable chambers and a rotating valve as a filling manifold may be provided. The device is made of a flexible material and is provided in a substantially deflated state, such that it is maneuverable and takes up a relatively small area. Prior to insertion, the device is rolled or folded in such a manner as to allow its delivery using minimally invasive surgical equipment such as tubes or cannulas. The device is inserted into the cavity of the patient and positioned within the patient using radiography or other visualization techniques.

All of the chambers are then filled through a single rotating valve having holes corresponding to openings in each of the chambers. The rotating valve is positioned such that holes in the valve align with openings in the chambers. Then, a fast resorbing reverse phase hydrogel is inserted through the valve (in liquid form), such that the liquid form of the gel flows into each of the chambers.

A pressure gauge on the device or a transducer capable of transmitting a signal to a remote device, indicates to the physician when the chambers have been filled to a desired amount, such that the surgeon stops the flow of the filler material into the chambers after the desired pressure is reached. It is contemplated that the filling (or stoppage thereof) may be somewhat automated, such that filling stops automatically upon a pressure or volume range reaching a pre-set level. Filling may also be stopped by rotating the ball valve 90 degrees to a closed position such that the holes of the ball valve are no longer aligned with the chambers. Regardless of how filling is actually stopped, the chambers are sealed after filling to prevent leakage of the filler material out of the chambers.

The hydrogel filler material gels upon reaching body temperature. Any load placed on the device may be distributed or shared among the different chambers.

Although the invention has been described in example specific embodiments, many additional modifications and variations would be apparent to those skilled in the art. For example, many modifications may be made by those skilled in the art to the example devices, including for example to the number, size, shape and placement of various chambers, as well as the type, number and configuration of filling manifolds. Other modifications may be made for example to the methods, including the addition of or changing the order of various steps. It is therefore to be understood that the invention may be practiced other than as specifically described. Thus, the present embodiments should be considered in all respects as illustrative and not restrictive.

What is claimed is:

1. An inflatable balloon device for use in a spine comprising at least three independent, adjacent hollow tube chambers, wherein each tube is curved to form a ring and the rings are arranged concentrically around an axis, substantially in a plane perpendicular to the concentric axis; and at least one filling manifold adapted to allow a filler material to be inserted at least partially concurrently into at least two of said at least three hollow tube chambers; wherein said inflatable balloon device is adapted to distribute load placed on the inflatable balloon device after filling, across multiple of the at least three hollow tube chambers wherein said device further comprises a sheath encasing said chambers and said filling manifold.

2. The inflatable balloon device of claim 1, further comprising a filler material within at least one of said at least three tube chambers, wherein said filler material is at least one material selected from the group consisting of gas, liquids, semi-liquids, and semi-solids.

3. The inflatable balloon device of claim 2, wherein said filler material is at least one material selected from the group consisting of hydrogel, air, water, and saline.

4. The inflatable balloon device of claim 1, further comprising a pressure detector within at least one of said chambers.

5. The inflatable balloon device of claim 1, further comprising at least one dye selected from the group consisting of a radiolucent dye and a radiopaque dye.

6. The inflatable balloon device of claim 1, further comprising a sealing means to prevent filler material from entering or exiting at least one of the chambers.

7. The inflatable balloon device of claim 6, wherein the sealing means is selected from the group consisting of heat, a mechanical plug, chemical means, a one way check valve, and friction.

8. The inflatable balloon device of claim 1, wherein said at least three chambers are surrounded by a reinforcing material.

9. The inflatable balloon device of claim 1, wherein said device is adapted for at least one of the following: replacement or augmentation of nucleus pulposus; distraction of neighboring vertebral elements; cushioning in a joint replacement system; plastic surgery augmentation, reconstruction, restoration, or tissue expansion; and damping, positioning, or isolation in a mechanical system.

10. A kit comprising the inflatable balloon device of claim 1, further comprising at least one additional component selected from the group consisting of: a device for inserting said inflatable balloon device into a patient in need thereof; filler material; a device for inserting filler material into the inflatable balloon device; at least one component for visualizing said device within a patient; and at least one component for determining when a desired filling point has been achieved.

11. A system comprising the inflatable balloon device of claim 1; and a filler material.

12. The system of claim 11, further comprising a high pressure gun for inserting the filler material into at least one of the at least three chambers.

13. A method of treating a patient comprising: inserting the inflatable balloon device of claim 1 into a patient in need thereof, wherein the device is a deflated state upon insertion into the patient; and inflating the device by inserting a filler material into at least one chamber of the device.

14. The method of claim 13, wherein the filler material is inserted with a high pressure gun.

15. The method of claim 13, further comprising sealing the inflated device, wherein said sealing is selected from the group consisting of heat, mechanically plugging, chemically sealing, friction, and closing the at least one rotating ball valve.

16. The method of claim 13, wherein said inflatable balloon device is inserted into a patient through a tube or cannula.

17. A method of removing a device according to claim 1 from a patient comprising removing filler material from the device in the patient to deflate the device; and extracting the deflated device from the patient.

18. A nucleus replacement device for use in a spine comprising: a multi-chambered inflatable balloon having at least three independent adjacent hollow tube chambers comprising a flexible material, wherein each tube is curved to form a ring and the rings are arranged concentrically around an axis, substantially in a plane perpendicular to the concentric axis; at least one filling manifold adapted to allow a filler material to be inserted at least partially concurrently into at least two of said hollow chambers via the filling manifold; a pressure detector positioned within at least one of said chambers, said pressure detector being adapted to detect pressure within at least one of said chambers; and a sealing means to prevent the filler material from entering or exiting at least two of the chambers.

19. The nucleus replacement device of claim 18, wherein said at least one filling manifold is selected from the group consisting of at least one valve and at least one tube.

20. The nucleus replacement device of claim 18, said device further comprising a sheath encasing said chambers and said manifold.

21. The nucleus replacement device of claim 18, wherein the sealing means is selected from the group consisting of heat, a mechanical plug, chemical means, a one way check valve, and friction.

22. The nucleus replacement device of claim 18, wherein said chambers are surrounded by a reinforcing material.

23. An inflatable nucleus replacement device for use in a spine comprising: a multi-chambered inflatable balloon comprising at least three independent, adjacent, hollow tube chambers comprising a flexible polymer material, wherein each tube is curved to form a ring and the rings are arranged concentrically around an axis, substantially in a plane perpendicular to the concentric axis; at least one filling manifold adapted to allow a filler material to be inserted at least partially concurrently into at least two of said at least three independent, adjacent, hollow tube chambers; and a pressure detector positioned within at least one of said chambers, said pressure detector being adapted to detect pressure within at least one of said chambers; wherein said inflatable nucleus replacement device is adapted to distribute load placed on the inflatable nucleus replacement device after filling, across multiple of the at least three chambers.

* * * * *